United States Patent [19]

van der Jagt

[11] Patent Number: Plant 5,955

[45] Date of Patent: Apr. 21, 1987

[54] CHRYSANTHEMUM PLANT NAMED FUNNY REDEMINE

[75] Inventor: Martinus van der Jagt, Ter Aar, Netherlands

[73] Assignee: Chrysathemum Breeders Association N.V., Curacao, Netherlands Antilles

[21] Appl. No.: 697,868

[22] Filed: Feb. 4, 1985

[30] Foreign Application Priority Data

Feb. 9, 1984 [NL] Netherlands ..... CHR 862

[51] Int. Cl.[4] ..... A01H 5/00

[52] U.S. Cl. ..... Plt./77

[58] Field of Search ..... Plt./77

*Primary Examiner*—Robert E. Bagwill

*Attorney, Agent, or Firm*—Parkhurst & Oliff

[57] ABSTRACT

A new and distinct cultivar of Chrysanthemum plant named 'Funny Redemine', bearing medium sized creamy-white blooms with a red center and having a performance of twenty days.

2 Drawing Figures

BACKGROUND OF THE NEW PLANT

The new plant of the present invention relates to the Chrysanthemum genus.

ORIGIN AND HISTORY OF THE PLANT

The new plant according to the present invention comprises a new and distinct cultivar of Chrysanthemum plant which is a color mutant of Chrysanthemum named 'Redemine'. The new cultivar was discovered by Martinus van der Jagt in 1982 at Paradijsweg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a medium sized bloom and creamy white color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the full bloom of the new cultivar;

Sheet 2 shows the foliage and petiole of the new cultivar.

DESCRIPTION OF THE NEW PLANT

This new variety of Chrysanthemum is of the botanical classification *Chrysanthemum morifolium,* named 'Funny Redemine'. When grown in the vicinity of Ter Aar, Holland, it has a response time of approximately ten to eleven weeks. This new variety produces medium sized creamy-white blooms with a red center having a performance of twenty days. This new variety of Chrysanthemum has been found to retain its distinctive characteristics throughout successive propagations and may be planted under conventional greenhouse conditions in Holland between weeks 01–34.

The following is a description of the plant and characteristics that distinguish it over related known varieties and its antecedents:

Botanical classification: *Chrysanthemum morifolium.*

Bud:

*Size.*—Medium, cross sect. 1.5 cm, height 1.3 cm.

*Form.*—Round and high.

*Color.*—Chartreuse green RHS 663/3.

Bloom:

*Size.*—Medium.

*Fully expanded.*—6–7 cm.

*Borne.*—Single.

*Stems.*'Strong (thick).

*Forms.*—Multple short tubular petals (decorative).

*Permanence.*—Good, 20 days (at 18°–20° C.).

Color:

*Center of flower (Disk Floret).*—Red RHS 19/2.

*Base of petals.* ≦White with a tint of Naples Yellow RHS 403/3.

*Inside of petals.*—White with occasionally at the top of the petals, RHS 23/3.

*Reverse of petals.*—White with occasionally at the top of the petals, RHS 23/3.

*Outer petals.*—White, RHS 155.

*Tonality from a distance.*—Small decorative with tubular petals of a creamy white color and a red spot in the center.

*Discoloration.*—To creamy white all over the flower (white with a tint of Naples Yellow RHS 403/3).

Petals:

*Texture (upper and underside).*—Rough and hard.

*Number.*—In excess of 150 including center.

*Cross-section.*—Tubular.

*Arrangement.*—Imbricated.

*Persistance.*—Strong, do not flex when overbloomed.

*Fragrance.*—Normal for Chrysanthemum.

Reproductive organs:

*Stamens.*—Small.

*Pollen.*—Does not appear when blooming.

*Styles.*—Columnar and thin.

*Length.*—Medium, 7 mm long.

*Stigmas.*—Very small, green RHS 61/2, width 0.5–1.0 mm.

*Ovaries.*—Enclosed in calyx.

Plant:

*Form.*—Single stem spray for erect cultures.

*Growth.*—Vigorous.

*Height.*—Tall, approx. 110 cms.

*Peduncle.*—Strong. Near the top — 7 cm. In the middle — 15 cm. Near the bottom — 21 cm.

*Internodes.*—3½–4 cm.

*Flowering response.*—10 to 11 weeks.

Foliage:

*Color.*—Willow green RHS 000862.

*Size.*—Length 13 cm, width 8 cm.

*Quantity.*—Between 28–32.

*Shape.*—Pointed oval.

*Texture.*—Leaves are soft and smooth. Upperside: Smooth, heavy layer of hair. Underside: Smooth, heavy layer of hair.

*Ribs and veins.*—Developed in normal quantity. Upperside: Ribs pronounced, veins very fine. Underside: Ribs pronounced, veins very fine.

*Edge.*—Undulated.

*Leaf underside.*—Smooth, heavy layer of hair.

In the description above, color references are made to the "Horticultural Color Chart I & II" issued by the British Colour Council in collaboration with The Royal Horticultural Society, Copyright Robert F. Wilson, Vol I, 1938; Vol II, 1941, printed by Henry Stone & Son, Ltd., Banbury, England.

What is claimed is:

1. A new and distinct cultivar of Chrysanthemum named 'Funny Redemine', as described and illustrated in the foregoing specification and accompanying drawings.

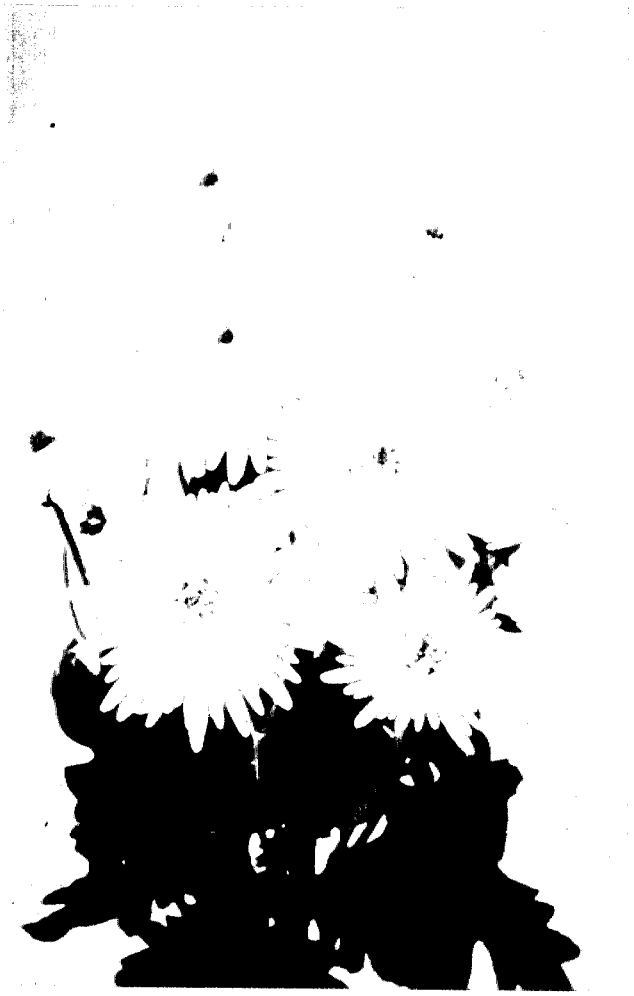

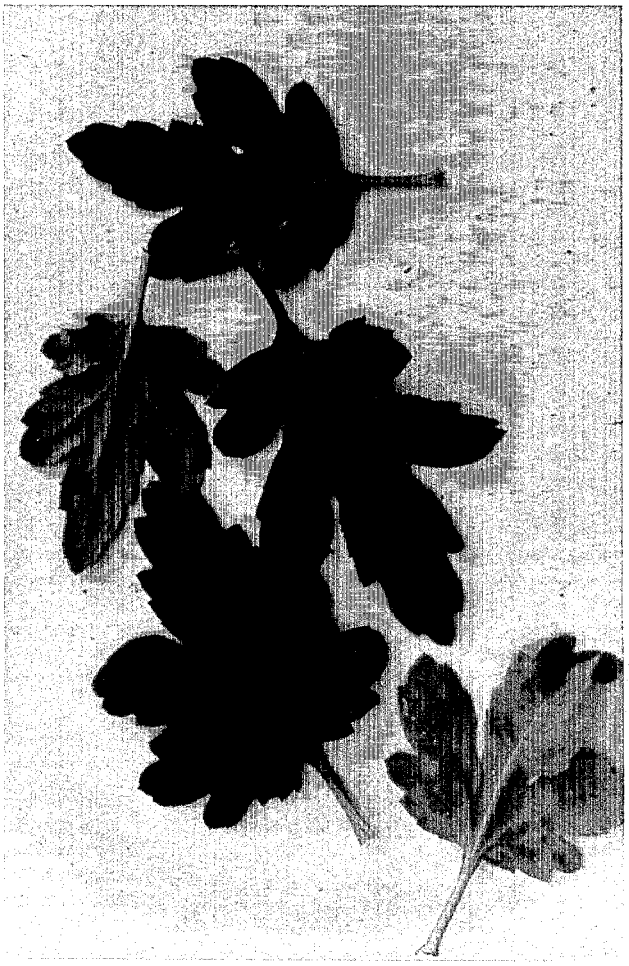

* * * * *